United States Patent [19]

Higgins et al.

[11] 4,451,364
[45] May 29, 1984

[54] HIGH PRESSURE SEAL AND COUPLING

[75] Inventors: Jeremy W. Higgins, Los Altos; Robert Brownlee, Los Altos Hills, both of Calif.

[73] Assignee: Brownlee Labs Inc., Santa Clara, Calif.

[21] Appl. No.: 354,395

[22] Filed: Mar. 3, 1982

[51] Int. Cl.³ .............................................. B01D 15/08
[52] U.S. Cl. ................................... 210/198.2; 55/386; 285/109; 285/177
[58] Field of Search ..................... 210/656, 659, 198.2; 55/386; 285/109, 177, 80

[56] References Cited

U.S. PATENT DOCUMENTS

| | | | |
|---|---|---|---|
| 3,422,604 | 1/1969 | Haase | 55/386 |
| 3,679,237 | 7/1972 | De Angelis | 285/109 |
| 3,878,099 | 4/1975 | Ogle | 55/386 |
| 3,904,527 | 9/1975 | Wilhelmson | 210/198.2 |
| 4,002,186 | 1/1977 | Fink | 285/80 X |
| 4,313,828 | 2/1982 | Brownlee | 55/386 |

Primary Examiner—John Adee
Attorney, Agent, or Firm—Robert B. Block

[57] ABSTRACT

A coupling for high pressure liquid chromatographic columns of any length, individually, or by union of two columns together, in which an end fitting carries a secondary seal together with internal means for retaining the seal in place. The end fitting is designed as a unitary assembly wherein the secondary seal is secured into the end fitting as a unitary assembly of parts without the use of screw threaded members. A special screw and nut configuration of end fittings permits the same design to be used for columns of extremely short lengths.

5 Claims, 6 Drawing Figures

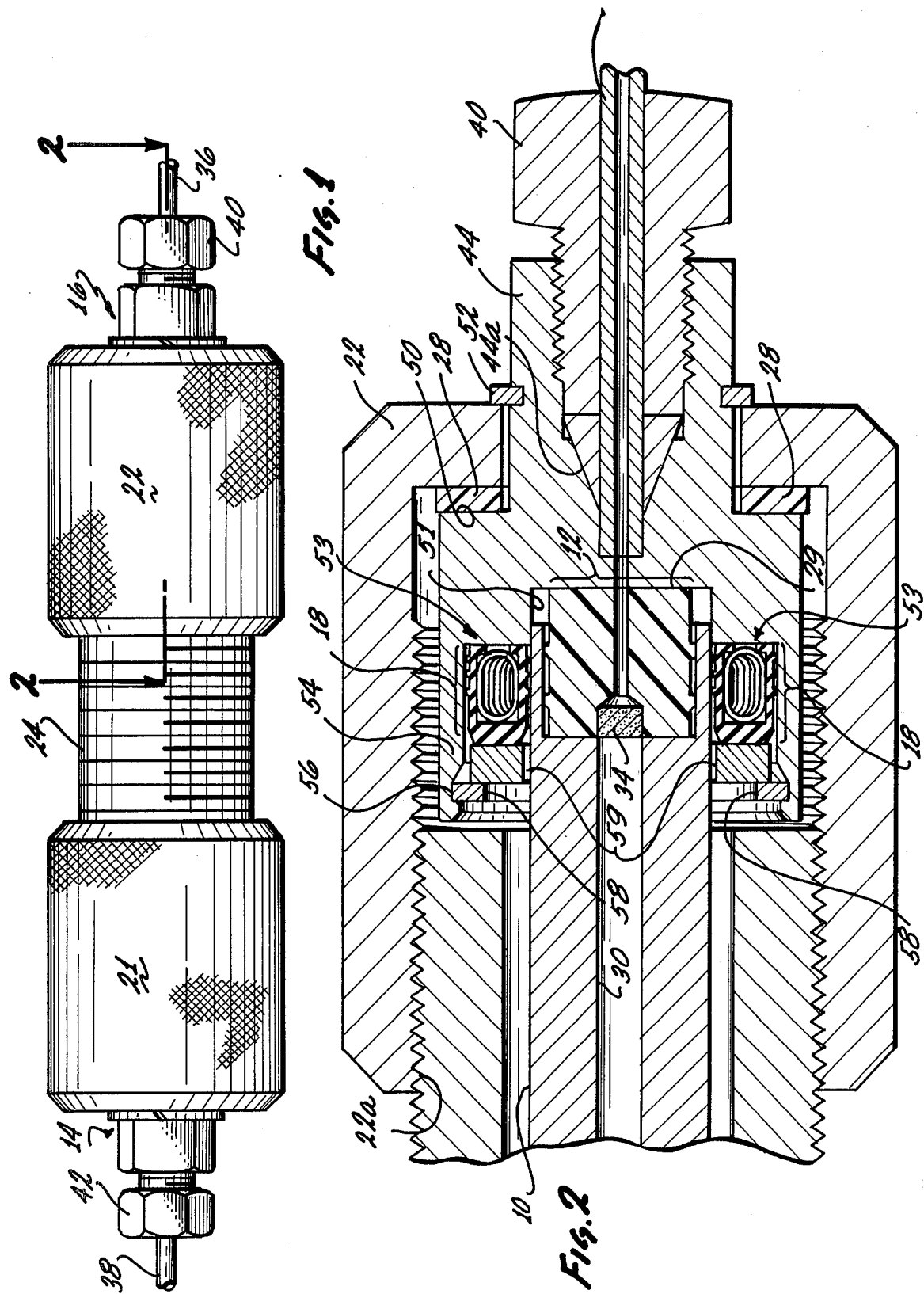

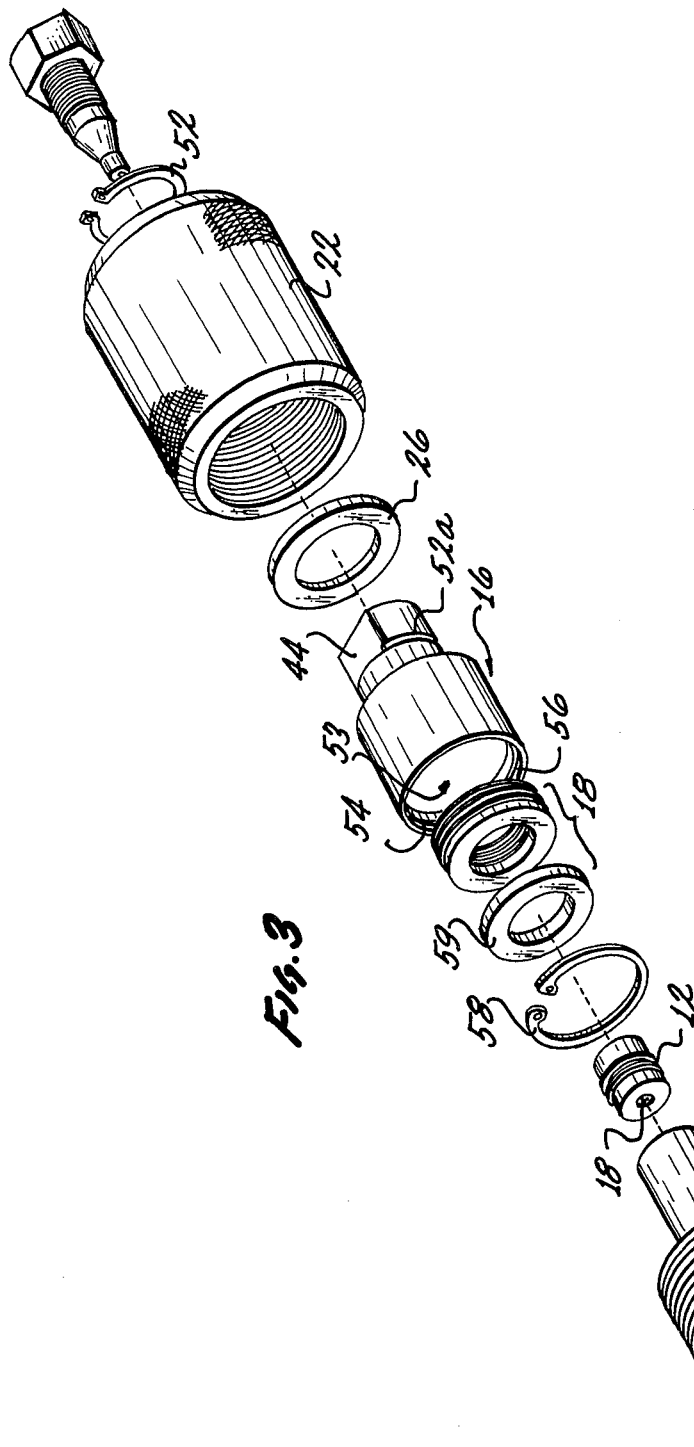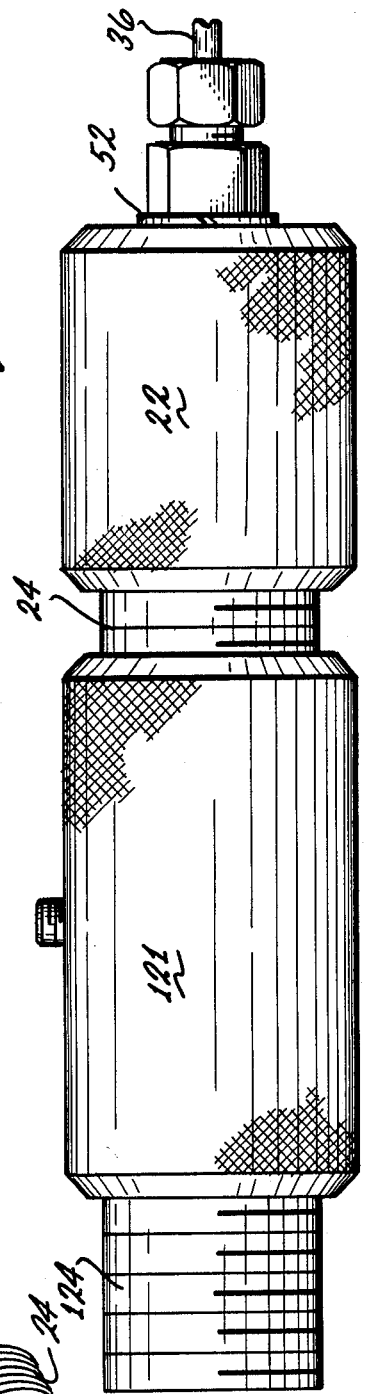

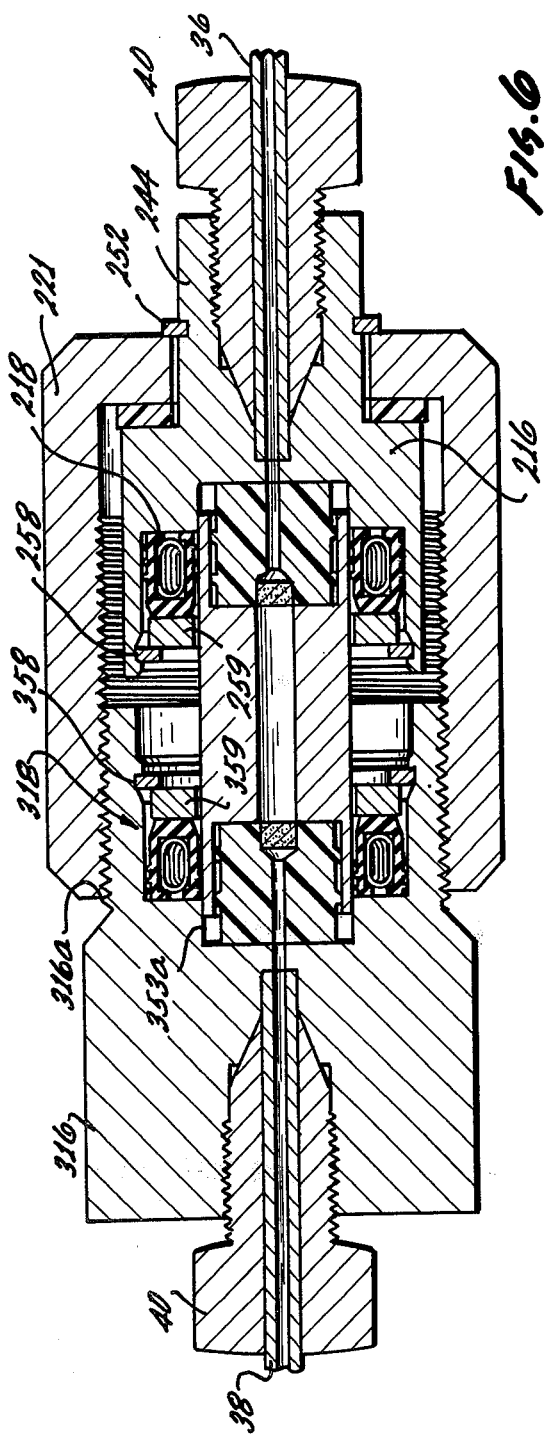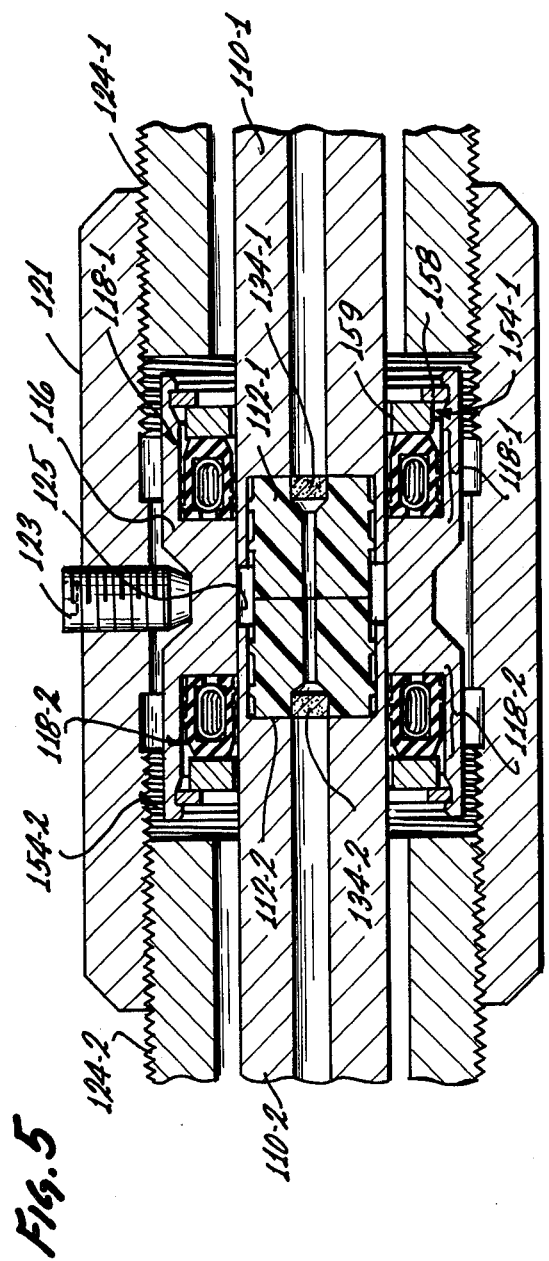

HIGH PRESSURE SEAL AND COUPLING

BACKGROUND OF THE INVENTION

This invention relates to high pressure liquid couplers and seals and more particularly to such couplers and seals as are used in liquid chromatography wherein it is desired to connect an elution column to a liquid chromatographic pumping system. More particularly, the invention relates to an improved tubing coupling system having easily replaceable parts for use in HPLC systems of the type disclosed in U.S. Pat. No. 4,313,828.

Generally, the invention can be applied as a coupler or union in any high pressure liquid pumping system in which it is required to assemble and tighten, by hand, a union or seal of low dead volume for easy replacement.

Definitions

The abbreviation HPLC shall mean high pressure liquid chromatograph(y) and may be used interchangeably therewith. HPLC indicates operation of an LC elution column with pressures substantially higher than 500 psi and generally in the range of 3,000 to 10,000 psi. LC shall mean liquid chromatograph(y) and may be used interchangeably therewith. Tube or tubing shall include pipe and piping and may be used interchangeably with each other and with the latter. An LC elution column includes a system of tubing and is included within the foregoing definition of tube, tubing, pipe, and piping. As used herein, the word coupler is meant in its generic sense and shall include union, or any form of distribution system having a port or pipe from which or to which liquid under high pressure is being delivered or received. If intended to more specific, another expression, such as union, will be used. Zero dead volume refers to a condition by which fluid passing through a channel bore or passageway is confined to flowing motion and has no way to enter into a space or volume in which no flow occurs and from which it could gradually reenter the column and adversely affect the separation process. This process depends on differential migration of components in a mobile phase passing through the column and must be capable of being cleared completely between samples. As used herein, zero dead volume does not preclude leakage from the means for achieving the same.

In the referenced U.S. Pat. No. 4,313,828, an end fitting was described as having a body portion for closely fitting to the end of an HPLC tubular column opening into a bell portion for receiving a secondary seal surrounding and coupling between the bell and the column outer wall. The secondary seal is of the hydraulic seal type in which liquid leakage under high pressure fills it into hydraulic operation. A shank at the other end of the end fitting is coupled to a small bore tubing which is connected to the LC system. Means is provided for coupling the fitting to the elution column and urging the same into compression against its first seal, the latter being disclosed as a knurled nut having one end partially to the elution column and urging the same into compression against its first seal, the latter being disclosed as a knurled nut having one end partially closed so as to abut against and bear against the shank when the same is screwed to a column holder. The column holder is symmetrical at the opposite end, so that when both ends are taken up, the elution column and first seals are compressed between them.

The foregoing basic arrangement has been found very satisfactory in operation. However, the details of carrying out the internal support of the elements to permit relatively easy column removal and replacement, and for change of seal elements has relied on structural arrangements having certain disadvantages. In order to allow the parts to rotate, that structure called for the secondary seal to be retained in the end fitting by an exteriorly threaded ring carried by the cap nut, and screwed into a critical position relative to the interposed end fitting just clearing the end fitting and the contained seal.

The seal clearances had to be close enough to prevent extrusion of the seal under high pressures, but sufficient to permit a swivel or rotation action between the nut and the end fitting. Whenever insufficient clearance was provided, rotation of the nut would twist the capillary tubing to which the end fitting was attached, and too great a clearance caused failure of the secondary seal at high pressures because of deformation by extrusion. The retaining ring was held in position with a plastic adhesive compound such as Loctite (TM). Replacement of the seal necessitated breaking the adhesive sealing contact between the retaining ring and the nut. This was difficult in view of the small size of the parts. The hydraulic seal member could then be removed with a dummy plug which inserted into the seal and used to pry it out of the end fitting. This required a separate seal replacement kit to be supplied which was unhandy to store, difficult to use, and was so infrequently needed that complete replacement of the seal assembly might be warranted as an alternative. Further, not only was the operation manually difficult for the user, but it also required the user to reassemble the seal with similar clearances to that obtained in original manufacture. The latter requirement was not often achieved in practice.

It would be desirable to have a seal of the same general structure and character as that disclosed in the aforementioned application, but constructed and arranged to provide a substantially easier manufacture and replacement feature. There is, therefore, a need for a new and improved coupling for liquid tubing applications.

SUMMARY OF THE INVENTION AND OBJECTS

A general object of the invention is to provide a coupling and seal for a high pressure tubing coupling which will overcome the above limitations and disadvantages.

A further object of the invention is to provide a coupling and seal assembly for a high pressure tubing which works on the same principle as that set forth in U.S. Pat. No. 4,313,828, but is mechanically arranged for ease of manufacture, disassembly and replacement of parts.

A further object of the invention is to provide a coupling and seal of the above character employing an end fitting which is self supporting and self contained with the seal, and structured as a replaceable unit.

A further object of the invention is to provide a seal mounted coupling of the above character which is a self contained unit from which the seal cannot be extruded from its position in operation, which can be replaced in its entirety when seal replacement is required.

A further object of the invention is to provide a seal mounted coupling of the above character which can be interchanged for the original parts described in U.S. Pat. No. 4,313,828.

A further object of the invention is to provide a seal mounted coupling of the above character which is constructed as a unitary assembly without requiring the use of any adhesives or glued parts.

Another object of the invention is to provide a seal and coupling of the above character which is particularly adapted to replace existing structures wherein a unit is placed in end-to-end compression within a self contained structure, or, is placed in abutting relationship with a like unit. Alternatively, an additional structure is provided which permits the unit to be reduced to practice in a form similar to a pipe union in which one portion remains stationary and the other portion is freely rotatable with respect thereto, the contained column cartridge being correspondingly reduced.

The foregoing objects are achieved in accordance with the present invention by reconstruction and redesign of the end fitting. Thus, the end fitting has one end in fluid communication with the tubing of an HPLC pumping system and the other end opening into a bell forming a chamber for receiving one end of an elution column. The column is terminated at each end with a plastic primary seal and is disposed within the end fitting chamber to form a zero dead volume seal recess. An annular recess is formed in the end fitting to surround the column tube and contains a secondary seal of a balanced hydraulic type. This hydraulic seal is in contact with and bounded by transverse bottom wall and a surrounding circumferential cylindrical wall of this annular recess. The balanced seal opens into fluid communication toward the primary seal and is operated by leakage from the same. The end fitting extends axially beyond the balanced seal in a continuation section of the bell end. A second recess of groove is formed adjacent the open end of one bell for receiving retaining ring means including a washer for holding the balanced seal in position. Thus, the retaining ring is set into the groove and positioned into the end fitting itself, the clearances between the several parts being established by their dimensions to provide satisfactory operation. No sliding friction will be encountered by the secondary seal during take-up of the coupling of this design in contrast with the couplings of U.S. Pat. No. 4,313,828. The end fitting itself is mounted for rotation between a spacing washer carried on its shank against which the cap nut bears to secure the same. A snap ring is located also on the shank on the other side of the cap nut for retaining the same in position while permitting such free rotation.

The invention is easily implemented in a form for coupling a tubing to a column from one end, which construction may be symmetrical in a compression arrangement, as is known.

In addition, the coupling provides for a simple end-to-end union of columns.

Another, shortened construction uses an asymmetrical arrangement particularly adapted for the use of extremely small guard columns, one side forming a nonrotating male screw member which directly couples into a rotating collar or nut serving as a female member of the pair. The latter construction permits reducing the column length to a short value as may be desired from other considerations while retaining all the advantages of the present invention and the structural and sealing integrity of structures of the general type disclosed herein and in U.S. Pat. No. 4,313,828.

These and other features and objects of the invention will become apparent from the following description when taken in conjunction with the accompanying drawings of which:

BRIEF DESCRIPTION OF THE DRAWINGS

FIG. 1 is a side elevational view of a seal and coupling assembled with a cartridge holder and constructed in accordance with the present invention.

FIG. 2 is a cross-sectional view taken along lines 2—2 of FIG. 1.

FIG. 3 is an exploded view in perspective of the disassembled parts of the coupling of FIGS. 1 and 2.

FIG. 4 is an elevational view of a combination union and coupling useful for adding a guard column to an HPLC column and constructed in accordance with the present invention.

FIG. 5 is a cross-sectional view taken along lines 5—5 of FIG. 4.

FIG. 6 is a cross-sectional view of a modified union coupling of cap screw construction without the use of a cartridge barrel for carrying tension load from end to end of the structure, the same functions being incorporated within the coupling parts themselves and constructed in accordance with the present invention.

DETAILED DESCRIPTION OF THE PREFERRED EMBODIMENTS

Column Seal and Coupling—General

Referring generally to FIGS. 1-3, a form of the invention is illustrated which directly replaces the end fitting shown and described in U.S. Pat. No. 4,313,828. Thus, an elution column is provided including a tube 10 closed at each end by a plug 12 forming a self contained replaceable cartridge and is disposed within a pair of end fittings 14,16 each including a liquid operated secondary seal assembly 18. The secondary seal assembly 18 is of the spring loaded, hydraulic seal type. Cap nuts 21,22 take up on a screw barrel 24 and interposed low friction washers and of Delrin acetal plastic to place the end fittings and cartridge in compression wherein the plugs abut the end fittings to form an operative primary seal at surfaces 29. In the embodiment of FIGS. 1-3, the column, the holder, and all the parts are symmetrical and identical so that the description herein will be given with reference to one end as shown in greater detail in FIGS. 2 and 3. This description should be understood to include both ends.

The cartridge is provided with an elongate bore 30 packed with a suitable sorbent material (not shown) such as a silica gel or other known particulate packing. End plugs 12 may be made of polytetrafluoroethylene, or other suitable plastic and serve to retain the packing within the cartridge bore; to carry a frit filter 34 for preventing particulate and chemical contamination of certain materials to which such columns are susceptible. The plug 12 also provides the primary cartridge seal when placed in compression. The specific structure shown in the present application is more fully described in our copending application entitled REPLACEABLE CARTRIDGE FOR LIQUID CHROMATOGRAPH, Ser. No. 354,394, filed concurrently herewith. While the structure shown in the cross-referenced application is to be preferred, it should be understood that the construction of a column cartridge set forth in U.S. Pat. No. 4,313,828 is also satisfactory and may be used interchangeably.

Referring particularly to the exploded portions of FIG. 3 and to the detailed assembly drawing of FIG. 2, the end tubing 36 from an HPLC pump injection system, not shown, and the outlet tubing 38, to the remainder of the liquid chromatograph and detector, pass through compression drive nuts 40,42 and into capillary engaging portion of the respective end fitting which includes an outwardly facing internally threaded projection 44. Such connections are well-known and may include a tapered conical section such as 44a which cooperates with a conical compression ferrule (not separately shown) so that a seal is formed by radial compression. The details of this known construction are omitted for clarity.

The inward facing end of each cap nut 21,22 has a recess opening 21a,22a which is internally threaded to engage the cartridge barrel 24. The other end of the cap is closed except for a central passage through which the capillary tubing and projection 44 of the end fitting may pass.

Each end fitting is provided with a shoulder 50 which extends laterally from the projection 44 and against which the washer 28 is carried by the turning of the cap nut 22. A retaining ring 52 is captured in a groove on the projection 44 with sufficient clearance that the cap nut may freely rotate between ring 52 and the shoulder 50 to provide smooth, swivel action. The arrangement is such that the end fitting is free to rotate without contact by any other part other than the rotational contact between the fluid seal ring assembly 18 with the wall of the tube 10 and the compression between the surface 29 and plug 12.

The structure of the fluid ring seal 18 has been previously described in U.S. Pat. No. 4,313,828 and is incorporated herein by reference together with the structural details and explanation of operation, which remains the same. While the seal 18 is essentially unchanged, its mounting and retention within the end fitting has been completely revised by rearrangement of the parts.

Referring specifically to FIGS. 2 and 3, the end fitting is enlarged at 53 to form an annular recess for seal 18 and opens outwardly in an extension 54 beyond the seal assembly 18. This extension is provided with an inwardly facing groove 56 which receives a retaining ring 58 which may be of the snap variety. Interposed between the ring 58 and the seal 18 is a retaining washer 59 which serves to substantially fill the gap between the tube and side wall of the recess of the fitting so that extrusion of the seal under pressure is not possible. These parts may be assembled with zero clearance. Accordingly, the several parts, the ring, the washer and the structure of the recess, together define means for retaining the seal 18 in the end fitting as a unitary assembly so that the end fitting, the seal assembly 18, the washer 59 and retaining ring 58 are coupled together, operate and are replaceable as a unit.

In accordance with this construction, it has been found feasible to eliminate for the user all mechanisms which were previously required to remove and replace the seal 18. It is now economic to merely provide a replacement end fitting and seal already assembled, as compared to the previous substantial cost of supplying the mechanical tools for removing and replacing seals. In addition, the present assembly has been achieved without the use of threaded parts so that its clearance and assembly are assured from the mechanical manufacturing tolerances. This results in a considerable advantage in ease of replacement and also in ease of interchanging columns since no connection is maintained between the cap nut and the end fitting relates to the seal assembly. Accordingly, it is no longer possible for slight changes in the seal configuration, due to small extrusions, to prevent or hinder rotation of the cap nut, or to cause difficulties and readjustment of the means for holding the seal 18 into position. Also, the cause of the previously experienced difficulties in removing the screw-threaded retaining ring from the cap nut during replacement has also been eliminated.

The following materials are preferred for construction of the present invention.

| | |
|---|---|
| Tube 10 | 316 stainless steel. |
| Plug 12 | Polytetrafluoroethylene or Polyfluoropropylene |
| End Cap 22 and Barrel 24 | Aluminum |
| Retaining Ring 58 | Stainless Steel |
| Washer 59 | Stainless Steel |
| End Fitting 16 | Stainless Steel |
| Retaining Ring 52 | Stainless Steel |

It will be noted that all of the parts associated with seal retention in the end fitting are made of stainless steel while the cap nut and barrel are made of aluminum. These are interconnected via plastic washer 26. There are no threaded interconnected parts between those elements which are stainless steel and those which are aluminum. For smoother operation the aluminum parts have been given a surface incorporated coating of Teflon (trademark) in the process of being anodized.

Guard Column and Union

While the seal of the present invention is particularly useful for both the analytical column mounting and for the guard column mounting of such systems, its simplicity and interchangability of replaceable parts make it easy to use and reuse in a wide variety of applications wherein a guard column is also desired. The latter can be provided either in a union assembly with an analytical column, to be described, or in a separate specialized column mounting, which will also be described, having substantially fewer parts but having the same functions. Guard columns have generally been made about 2 to 3 centimeters in length in order to provide adequate removal of impurities and for a given useful lifetime. The three centimeter length in the past has been a compromise length which is long enough to permit ease of hand-tightening. The present invention permits substantially smaller lengths to be used.

Referring to FIGS. 4 and 5, a union constructed in accordance with the teachings of this invention is disclosed and is particularly adapted to utilize common elements at its center of construction whereby a guard cartridge and an analytical cartridge may be directly joined together without any intervening parts or plumbing. This has a particular advantage in the capability of providing for the addition of a guard column while having a minimum of degrading effects on the performance of the system. Where like parts have been used in the union, they have been given the same identifying numbers as in FIGS. 1-4 raised by 100. More specifically, FIGS. 4 and 5 show a union fitting 116 having a smooth exterior for sliding into the interior of a knurled nut 121 which is interiorly threaded. As shown, a set screw 123 is employed to fix the relationship axially between the sleeve nut 121 and the fitting 116. A first recess for containing the column ends is defined by an inwardly extending annular projection of the fitting having a cylindrical bore 125 therethrough of a dimension similar to that described with respect to the wall 48 of the recess of the coupler of FIGS. 2 and 3. This bore is uniform through its length and sufficiently long to accommodate the end axial length of both ends of a pair of abutting end plugs of columns and a portion of the tubing of the respective columns themselves to provide lateral support. The dimensions are similar to those of FIGS. 2 and 3. However, the "floor" of each "recess" is defined in this instance by the opposite end plug of the adjacent abutting cartridge.

The structure of the balanced seals 118 and the annular recesses 153 in which they are retained is identical to that previously described with respect to the recesses 53 and seal 18. Thus, the fitting is formed with oppositely directed and outwardly oriented annular recesses 153-1,153-2 constructed in the manner of extension recess 53 including an outer lateral wall 180 and 181, floors 182 and 183 communicating with the side wall of the bore 125. The union fitting 116 extends axially beyond the respective ones of sealing rings 118 at 154 and is provided with means at each end for retaining within the union fitting itself the retaining rings 158 and washers 159 for forming the union into a self contained seal assembly without the need for associated parts as were previously known to be attached between the nuts 121 and barrel 124 and the device.

The assembly of this arrangement is quite simple since the overall dimensioning of the several parts will serve to locate to sufficient accuracy the region in which the ends of the columns are to abut. Thereafter, the compression is taken up and supplied by the remaining parts, and if necessary, rotation of the knurled nut may be employed if it is counter-threaded. Otherwise, if it is threaded uniformly, its rotation will have no effect on the compression in the system, the latter being strictly a function of the outer knurled nuts (not shown). More specifically, it is preferred that nut 121 serve as means for transmitting tension between the barrels 24 and 124 while the fitting 116 serves the function of maintaining all the parts centered and in an appropriate lateral orientation. Compression is thus transmitted directly from the analytical column on the one side to the guard column on the other side through the end nuts at opposite ends of the structure, and as tension through the barrels 24,124 and sleeve nut 121.

Ball and Nut Coupled Column

Referring now to FIG. 6, there is shown a cross-sectional view of a column which is ultrashort being particularly adapated for use with microbore columns. As is known, present technology favors the use of columns having a very small bore, requiring a corresponding reduction in the length of the guard columns. Such columns are often called microbore columns and may be as short as 1 centimeter in length. By reducing the physical size of the guard column system, the system variance can be reduced by a remarkable degree, perhaps by as much as a factor of 10. As mentioned in the referenced U.S. Pat. No. 4,313,828, a practical lower limit of about 2-3 centimeters for guard columns was previously known. It has now been found possible to reduce the guard column length to a centimeter or less, and, in fact, to just about any shortness of length desired, while maintaining all the features of the present invention. FIG. 6 shows such a construction in which the lefthand side has been replaced with a ball or screw construction not much larger than a large machine bolt wherein like parts are given like numbers to those of FIGS. 1-3 raised by a factor of 200. Thus, an end fitting 216 is shown together with a cap nut 221 and a seal ring assembly and retaining mechanism 218, 258, 259, all of which is assembled and constructed identically to that shown in FIG. 2. However, the mating section is revised considerably.

Thus, the end fitting itself has been reshaped and provided with external threads for being captured in the nut 221, this section being numbered the same as FIG. 1 with the addition of 300. Thus, end fitting 316 is the same exterior diameter as the interior of cap nut 221 and provided with interior threads 316a thereon for engaging the threads of the cap nut 221. An interior recess 351 is developed for receiving the end of column 310 which is provided with an annular recess 353 surrounding the same for receiving the seal assembly 318, the latter being held in place by washer 359 for shape retention and a retaining ring 358 set in a groove in the same manner as previously described. It will be noted that no swivel feature is required between any of the parts of the screw section numbered above 300 since in any union it is only actually necessary to provide a single swivelable part, this being already provided by the action of the parts bearing identification numbers 200, etc. Even though this system is asymmetrical, it only requires the stocking of a single additional assembly, that comprising elements 316, 318, 358, 359, all stainless steel, and is readily replaced as a unit.

Thus, there has been provided an exceptionally effective high pressure seal for use in liquid chromatography also shown is a revised assembly for employing a guard cartridge either as a union for direct connection to an existing analytical cartridge or as a separate structure where the guard cartridge may be made about as small as desired. To those skilled in the art to which the invention pertains, many modifications and adaptations will occur. Accordingly, the details of construction and assembly of the various embodiments set forth herein should be taken as an example of the invention, the scope of which should be determined solely by reference to the following claims.

We claim:

1. Apparatus for coupling a tubular column to a fluid carrying line comprising an end fitting including a body having a bell opening at one end forming a chamber for receiving the end of a tubular column, means connecting the other end of the fitting to the fluid line,
   a first seal interposed between the end of the column and the fitting,
   means forming a first annular recess formed interiorly in the chamber wall surrounding the column,
   a secondary seal of the hydraulic type disposed in said first recess and making circumferential sealing contact to the outer wall of the column,
   said end fitting bell having a continuing section extending beyond the first recess and secondary seal,
   means forming a second recess or groove formed interiorally in the continuing section,
   retaining ring means disposed in said second recess for securing said second seal in position against the secondary seal and against axial movement of the same.

2. Couping apparatus as in claim 1 in which said retaining ring means includes a snap ring and a retaining washer interposed between the snap ring and the secondary seal.

3. A liquid coupling as in claim 1 further in which said end fitting is provided with a shoulder thereon at the end of opposite said bell,
- means forming a threaded cap nut having an opening therein for passing the end of said end fitting to said shoulder,
- means forming a retaining ring groove on said end fitting at a position for capturing said cap nut for free rotation thereof,
- a retaining ring disposed in said last named groove.

4. A union fitting for joining two chromatograph columns end-to-end in an abutting connection at a junction comprising
- a pair of columns, a pair of column holders, sleeve means for interconnecting said holders at the junction, and means at the remote ends of said holders for placing the columns in end-to-end compression,
- a double end fitting surrounding said columns at said junction and having a central bore formed therein closely fitting to the columns, said double end fitting having at each end of its opposite ends a chamber for receiving respective one of said columns and including a bell opening at each end therein,
- each of said bell ends including a first annular recess formed in the chamber wall to surround said respective column,
- a secondary seal of the hydraulic type disposed in said recess and making circumferential sealing contact to the outer wall of the respective column,
- each said end fitting bell ends having a continuing section extending beyond the first recess and the secondary seal and in the direction of the respective sealed column,
- a second recess or groove formed interiorally of said continuing section,
- retaining ring means disposed in said second recess for securing said second seal in a position against the secondary seal and against axial movement of the same away from the junction.

5. A holder and seal assembly for placing a short column in fluid communication with a high-pressure line of an LC chromatograph comprising a union pair of members adapted to be threaded together,
- said first union member forming an exteriorly threaded end fitting for receiving one end of said short column,
- the other member of said union pair forming a nut having interior threads at one end for connection to said first member and generally closed at its other end for forming a passage for a portion of a second end fitting to pass therethrough for connection to the LC chromatograph line,
- each of said first and second end fittings being of the same general internal construction and comprising a first annular recess formed in the chamber wall surrounding the column,
- a secondary seal of the hydraulic type disposed in said recess and making circumferential sealing contact to the outer wall of the column,
- said end fitting bell having a continuing section extending beyond the first recess and secondary seal,
- a second recess or groove formed interiorly in the continuing section,
- retaining ring means disposed in said second recess for securing said second seal in position against the secondary seal and against axial movement of the same.

* * * * *